US011339129B2

United States Patent
Jewett et al.

(10) Patent No.: US 11,339,129 B2
(45) Date of Patent: *May 24, 2022

(54) TRIAZABUTADIENES AS CLEAVABLE CROSS-LINKERS

(71) Applicant: ARIZONA BOARD OF REGENTS ON BEHALF OF THE UNIVERSITY OF ARIZONA, Tucson, AZ (US)

(72) Inventors: John C. Jewett, Tucson, AZ (US); Flora W. Kimani, Tucson, AZ (US); Lindsay E. Guzman, Tucson, AZ (US); Brandon M. Cornali, Tucson, AZ (US)

(73) Assignee: ARIZONA BOARD OF REGENTS ON BEHALF OF THE UNIVERSITY OF ARIZON, Tucson, AZ (US)

( * ) Notice: Subject to any disclaimer, the term of this patent is extended or adjusted under 35 U.S.C. 154(b) by 679 days.

This patent is subject to a terminal disclaimer.

(21) Appl. No.: 16/321,605

(22) PCT Filed: Jul. 31, 2017

(86) PCT No.: PCT/US2017/044737
§ 371 (c)(1),
(2) Date: Jan. 29, 2019

(87) PCT Pub. No.: WO2018/023130
PCT Pub. Date: Feb. 1, 2018

(65) Prior Publication Data
US 2021/0002234 A1   Jan. 7, 2021

Related U.S. Application Data

(63) Continuation of application No. 15/427,988, filed on Feb. 8, 2017, now Pat. No. 10,125,105, which is a
(Continued)

(51) Int. Cl.
C07D 233/88 (2006.01)
A61K 47/54 (2017.01)
(Continued)

(52) U.S. Cl.
CPC .......... C07D 233/88 (2013.01); A61K 47/545 (2017.08); A61K 49/0021 (2013.01);
(Continued)

(58) Field of Classification Search
CPC ............ C08G 73/08; C08G 2261/3221; C08G 12/28; A61K 47/48; A61K 31/5575
See application file for complete search history.

(56) References Cited

U.S. PATENT DOCUMENTS 3,591,575 A  7/1971  Golda
3,607,542 A  9/1971  George et al.
(Continued)

FOREIGN PATENT DOCUMENTS

DE   265008 A1   2/1989
DE   4242428 A1  10/1993
(Continued)

OTHER PUBLICATIONS

Addy et al. 'A Chemoselective Rapid Azo-Coupling Reaction (CRACR) for "Unclickable" Bioconjugation', J Am Chem Soc. 2017, vol. 139(34), pp. 11670-11673. doi:10.1021/jacs.7b05125.
(Continued)

*Primary Examiner* — Shane Fang
(74) *Attorney, Agent, or Firm* — Nguyen Tarbet LLC

(57) ABSTRACT

Triazabutadiene molecules as cleavable cross-linkers adapted to cross-link components with click chemistry, e.g., clickable triazabutadienes. For example, in some embodiments, the triazabutadienes feature alkyne handles attached to the imidazole portion or the aryl portion of the triazabutadienes, wherein the alkyne handles can link to azide
(Continued)

handles (e.g., azide handles disposed on other components) via click chemistry. Also described are methods of producing said clickable triazabutadienes and methods of use of said clickable triazabutadienes. The present invention also features methods of cleaving said clickable triazabutadienes, e.g., for liberating the diazonium species for further chemical reactions.

8 Claims, 5 Drawing Sheets

Related U.S. Application Data continuation-in-part of application No. 15/317,894, filed on Dec. 9, 2016, now Pat. No. 10,047,061, and a continuation-in-part of application No. 15/224,446, filed on Jul. 29, 2016, now Pat. No. 9,593,080.

(51) Int. Cl.

| | |
|---|---|
| A61K 49/00 | (2006.01) |
| C07D 403/12 | (2006.01) |
| C07D 405/12 | (2006.01) |
| C07D 413/14 | (2006.01) |
| C07H 21/00 | (2006.01) |
| C09B 26/06 | (2006.01) |
| C09B 55/00 | (2006.01) |
| C09J 163/00 | (2006.01) |
| C09K 11/06 | (2006.01) |
| G01N 33/569 | (2006.01) |
| G01N 33/68 | (2006.01) |

(52) U.S. Cl.
CPC ......... *C07D 403/12* (2013.01); *C07D 405/12* (2013.01); *C07D 413/14* (2013.01); *C07H 21/00* (2013.01); *C09B 26/06* (2013.01); *C09B 55/003* (2013.01); *C09J 163/00* (2013.01); *C09K 11/06* (2013.01); *G01N 33/56983* (2013.01); *G01N 33/6845* (2013.01); *C09K 2211/1048* (2013.01)

(56) References Cited

U.S. PATENT DOCUMENTS

| | | | |
|---|---|---|---|
| 3,959,210 | A | 5/1976 | Lipatova et al. |
| 4,107,353 | A | 8/1978 | Gabriel et al. |
| 4,218,279 | A | 8/1980 | Green |
| 4,356,050 | A | 10/1982 | Crivello et al. |
| 4,602,073 | A | 7/1986 | Skoultchi et al. |
| 5,856,373 | A | 1/1999 | Kaisaki et al. |
| 8,603,451 | B2 | 12/2013 | Zhang et al. |
| 8,617,827 | B2 | 12/2013 | Hell et al. |
| 8,668,978 | B2 | 3/2014 | Malima et al. |
| 9,085,715 | B2 | 7/2015 | Berthelot et al. |
| 9,458,143 | B1 | 10/2016 | Jewett et al. |
| 9,593,080 | B1 | 3/2017 | Jewett et al. |
| 10,047,061 | B2 | 8/2018 | Jewett et al. |
| 10,125,105 | B2 | 11/2018 | Jewett et al. |
| 2002/0197439 | A1 | 12/2002 | Berneth et al. |
| 2004/0241205 | A1 | 12/2004 | Babich et al. |
| 2005/0080260 | A1 | 4/2005 | Mills et al. |
| 2007/0049587 | A1 | 3/2007 | Zbinden et al. |
| 2007/0098807 | A1 | 5/2007 | Babich et al. |
| 2007/0104719 | A1 | 5/2007 | Carter et al. |
| 2009/0048222 | A1 | 2/2009 | Bell et al. |
| 2009/0286308 | A1 | 11/2009 | Berthelot et al. |
| 2011/0245287 | A1 | 10/2011 | Holaday et al. |
| 2017/0114033 | A1 | 4/2017 | Jewett et al. |
| 2018/0230106 | A1 | 8/2018 | Jewett et al. |

FOREIGN PATENT DOCUMENTS

| | | |
|---|---|---|
| WO | WO 2008/090554 A2 | 7/2008 |
| WO | WO 2009/137916 A1 | 11/2009 |
| WO | WO2015073746 A2 | 5/2015 |
| WO | WO2015191735 A1 | 12/2015 |
| WO | WO2017027743 A1 | 2/2017 |
| WO | WO2017180889 A1 | 10/2017 |
| WO | WO2018023130 A1 | 2/2018 |
| WO | WO2018165666 A1 | 9/2018 |

OTHER PUBLICATIONS

Jensen et al. 'Light-Activated Triazabutadienes for the Modification of a Viral Surface', Chembiochem. 2016, vol. 17 (23), pp. 2216-2219. doi:10.1002/cbic.20160050B.

International Search Report Issued for PCT Application No. PCT/US19/13996 dated Apr. 29, 2019.

Arlett, J. L., Myers, E. B., & Roukes, M. L. (2011). Comparative advantages of mechanical biosensors. Nature Nanotechnology, 6(4), 203-215. http://doi.org/10.1038/nnano.2011.44.

Gooding, J. J., & Darwish, N. (2012). The rise of self-assembled monolayers for fabricating electrochemical biosensors—an interfacial perspective. Chemical Record, 12(1), 92-105. http://doi.org/10.1002/tcr.201100013.

Grieshaber, D., Mackenzie, R., Vörös, J., & Reimhult, E. (2008). Electrochemical Biosensors—Sensor Principles and Architectures. Sensors, 8(3), 1400-1458. http://doi.org/10.3390/s8031400.

Gwent Systems, G. A. M. (n.d.). Electrochemical Biosensor Materials. Retrieved from http://www.gwent.org/presentations/biosensors.pdf.

Jung, J., & Lim, S. (2013). ZnO nanowire-based glucose biosensors with different coupling agents. Applied Surface Science, 265, 24-29. http://doi.org/10.1016/j.apsusc.2012.10.069.

Mahouche-Chergui, S., Gam-Derouich, S., Mangeney, C., & Chehimi, M. M. (2011). Aryl diazonium salts: a new class of coupling agents for bonding polymers, biomacromolecules and nanoparticles to surfaces. Chemical Society Reviews, 40(7), 4143-4166. http://doi.org/10.1039/c0cs00179a.

Reyes De Corcuera, J., & Cavalieri, R. (2003). Biosensors. Encyclopedia of Agricultural, Food, and Biological Engineering, 119-123. http://doi.org/10.1081/E-EAFE.

Smith, R. K., Lewis, P. A., & Weiss, P. S. (2004). Patterning self-assembled monolayers. Progress in Surface Science, 75(1-2), 1-68. http://doi.org/10.1016/j.progsurf.2003.12.001.

Thévenot, D. R., Toth, K., Durst, R. A., & Wilson, G. S. (2001). Electrochemical biosensors: Recommended definitions and classification. Biosensors and Bioelectronics, 16(1-2), 121-131. http://doi.org/10.1016/S0956-5663(01)00115-4.

Kimani et al., Water-soluble Triazabutadienes that Release Diazonium Species upon Protonation under Physiologically Relevant Conditions, Angewandte Chemie International Edition, vol. 54, Feb. 6, 2015 (retrieved on Nov. 18, 2016). Retrieved from the Internet: <URL:http://onlinelibrary.wiley.com/doi10.1002lanie.201411277/abstract; jsessionid=878CB7308B68B03C6CDEA4579EA97B54.f03t01>. pp. 4051-4054.

Zhong et al., 2014, Nature Nanotechnology 9, 858-866.

Stewart et al., 2011, J Polym Sci B Polym Phys 49(11):757-771.

Poulsen et al., 2014, Biofouling 30(4):513-23.

Stewart, 2011, Appl Microbiol Biotechnol 89(1):27-33.

Stewart et al.,, 2011, Adv Colloid Interface Sci 167(1-2):85-93.

Hennebert et al., 2015, Interface Focus 5(1):2014.

Y. Modis, S. Ogata, D. Clements, S. C. Harrison, Nature 2004, 427, 313-319.

C. D. Blanchette, Y. H. Woo, C. Thomas, N. Shen, T. A. Sulchek, A. L. Hiddessen, PLoS One 2009, 4, e6056.

J. Han, K. Burgess, Chem. Rev. 2010, 110, 2709-2728.

J. Kalia, R. T. Raines, Angew. Chem. Int. Ed. Engl. 2008, 47, 7523-7526.

J. Kalia, R. T. Raines, Angew. Chem. 2008, 120, 7633-7636.

J. Z. Du, X. J. Du, C. Q. Mao, J. Wang, J. Am. Chem. Soc. 2011, 133, 17560-17563.

E. H. Cordes, H. G. Bull, Chem. Rev. 1974, 74, 581-603.

(56) References Cited

OTHER PUBLICATIONS

A. Luong, T. Issarapanichkit, S. D. Kong, R. Fonga, J. Yang, Org. Biomol. Chem. 2010, 8, 5105-5109.

Fanghänel, R. Hänsel, W. Ortmann, J. Hohlfeld, J. Prakt. Chem. 1975, 317, 631-640.

H.-T. Dorsch, H. Hoffmann, R. Hansel, G. Rasch, E. Fanghänel, J. Prakt. Chem. 1976, 318, 671-680.

E. Fanghänel, R. Hänsel, J. Hohlfeld, J. Prakt. Chem. 1977, 319, 485-493.

E. Fanghänel, H. Poleschner, R. Radeglia, R. Hänsel, J. Prakt. Chem. 1977, 319, 813-826.

E. Fanghänel, J. Hohlfeld, J. Prakt. Chem. 1981, 323, 253-261.

R. Radeglia, R. Wolff, T. Steiger, S. Simova, E. Fanghanel, J. Prakt. Chem. 1984, 5, 511-514.

E. Fanghänel, W. Ortmann, A. Hennig, J. Prakt. Chem. 1988, 330, 27-34.

E. Fanghänel, W. Ortmann, J. Prakt. Chem. 1989, 331, 721-725.

E. Fanghänel, J. U. Bauroth, H. Hentschel, F. Gußmann, H. Alzyadi, W. Ortmann, J. Prakt.Chem. 1992, 334, 241-247.

D. M. Khramov, C. W. Bielawski, Chem. Commun. 2005, 4958-4960.

S. Dahmen, S. Brase, Org. Lett. 2000, 2, 3563-3565.

S. Brase, Acc. Chem. Res. 2004, 37, 805-816.

D. Jishkariani, C. D. Hall, A. Demircan, B. J. Tomlin, P. J. Steel, A. R. Katritzky, J. Org. Chem. 2013, 78, 3349-3354.

D. M. Khramov, C. W. Bielawski, J. Org. Chem. 2007, 72, 9407-9417.

A. G. Tennyson, E. J. Moorhead, B. L. Madison, J. A. V. Er, V. M. Lynch, C. W. Bielawski, Eur. J. Org. Chem. 2010, 6277-6282.

W. Herrmann, C. Köcher, Angew. Chem. Int. Ed. 1997, 36, 2162-2187.

W. Herrmann, C. Köcher, Angew. Chem. 1997, 109, 2256-2282.

N. Marion, S. Díez-González, S. P. Nolan, Angew. Chem. Int. Ed. Engl. 2007, 46, 2988-3000.

N. Marion, S. Díez-González, S. P. Nolan, Angew. Chem. 2007, 119, 3046-3058.

A. F. Hegarty, in The Chemistry of Diazonium and Diazo Groups, vol. 2 (Ed.: S. Patai), John Wiley & Sons, Ltd., New York, NY, 1978, pp. 511-591.

L. P. Hammett, J. Am. Chem. Soc. 1937, 59, 96-103.

B. M. Tracey, D. E. G. Shuker, Chem. Res. Toxicol. 1997, 10, 1378-1386.

J. M. Hooker, E. W. Kovacs, M. B. Francis, J. Am. Chem. Soc. 2004, 126, 3718-3719.

J. Gavrilyuk, H. Ban, M. Nagano, W. Hakamata, C. F. Barbasiii, Bioconjugate Chem. 2012, 23, 2321-2328.

L. Wang, V. Gruzdys, N. Pang, F. Meng, X.-L. Sun, RSC Adv. 2014, 4, 39446.

European Journal of Inorganic Chemistry vol. 2013, Issue 12, p. 2020-2030, Apr. 2013 Elena García-Moreno, Elena Cerrada, M. José Bolsa, Asunción Luquin and Mariano Laguna.

European Journal of Medicinal Chemistry vol. 46, Issue 7, Jul. 2012, p. 2748-2758, Marijana Hranjeca, Borka Lučića, Ivana Ratkajb, Sandra Kraljević Pavelićb, Ivo Piantanidac, Krešimir Pavelićb, Grace Karminski-Zamola.

Phosphate-buffered saline (PBS) CSH Protocols. "http://cshprotocols.cshlp.org/content/2006/1/pdb.rec8247".

Cornaii, 'Development of Clickable Triazabutadienes as Cleavable Cross-linkers', A thesis submitted to the Faculty of the Department of Chemistry and Biochemistry in Partial Fulfillment of the Requirements for the Degree of Master of Science, the University of Arizona, Apr. 8, 2016.

International Search Report Issued for PCT Application No. PCT/US15/35136 dated Sep. 14, 2015.

International Search Report Issued for PCT Application No. PCT/US17/44737 dated Dec. 11, 2017.

International Search Report Issued for PCT Application No. PCT/US16/46624 dated Dec. 9, 2016.

Pubchem, SID 42688522, Dec. 5, 2007 [retrieved on Nov. 18, 2016].

International Search Report Issued for PCT Application No. PCT/US18/22046 dated May 22, 2018.

Guzman et al. Protecting Triazabutadienes to Afford Acid Resistance, ChemBioChem Sep. 23, 2016. vol. 17, p. 2220-2222.

Formula A

Formula B

Formula C 6 (TBD-6)   7 (TBD-7)

TRIAZABUTADIENES AS CLEAVABLE CROSS-LINKERS

BACKGROUND OF THE INVENTION

Triazabutadienes can be triggered to release a highly reactive diazonium species in a pH-dependent way when placed in acidic conditions. Electron-rich phenyl systems such as resorcinol or tyrosine residues can react with the diazonium compounds to form stable azobenzene products. Alterations of these triazabutadiene motifs allow for modification of functionality, solubility, and other molecular properties. For example, triazabutadienes can be modified to liberate the diazonium species, in some cases near a site of interest.

Inventors discovered triazabutadienes (e.g., a series of alkyne-containing triazabutadienes) that can be used for cross-linking a secondary component using copper (1) catalyzed azide alkyne cycloaddition. This was surprising because the nitrogen-rich scaffold of the triazabutadiene looks similar to a ligand for the copper (1), and thus it was expected that these triazabutadienes would become destroyed in the reaction with the copper (1) or would bind with the copper (1) to form an inactive complex. However, the alkyne-containing triazabutadienes of the present invention can survive the copper click reaction and shows no ligation with copper metal. For example, when reacting with p-cresol or bovine serum albumin (BSA), the aryl diazonium chemistry proceeded smoothly to give the desired products, providing a critical bridge between Cu-click chemistry with diazonium ions.

The present invention features triazabutadienes as cleavable cross-linkers, wherein the triazabutadienes allow for cross-linking with a secondary component via click chemistry (copper (1) catalyzed azide alkyne cycloaddition), e.g., "clickable" triazabutadienes. In some embodiments, the clickable triazabutadienes comprise or are linked to a first component (e.g., a protein, a drug, a surface, etc.) and via click chemistry said first component can be cross-linked to a second component (e.g., another protein, surface, etc.).

The present invention also features methods of producing said clickable triazabutadienes and methods of use of said clickable triazabutadienes. For example, the compositions of the present invention may be used as biological cross-linkers and methods of the present invention may be used for biological methods such as detecting protein-protein interactions, mapping drug-target interactions, discovering or characterizing host-pathogen interactions, etc. The present invention also features methods of cleaving said triazabutadienes, e.g., cleaving the clickable triazabutadienes that has undergone click chemistry and is in the cross-linking state. In some embodiments, cleavage of the cross-linking triazabutadiene liberates the diazonium species; thus, the present invention also features methods that feature diazonium reactions following cleavage of said linking triazabutadienes.

SUMMARY

The present invention features clickable triazabutadiene according to (a) Formula B wherein $X^1$ comprises a terminal alkyne handle; or (b) Formula C wherein either $X^1$ comprises a terminal alkyne, $X^2$ comprises a terminal alkyne handle, or both $X^1$ and $X^2$ comprise a terminal alkyne handle; wherein A=S, O, or N; D=H, —CH=CH—CH=E-, halides, cyano, sulfonates, alkyl chain, or trifluoromethyl; E=H, —CH=CH—CH=D-, halides, cyano, sulfonates, alkyl chain, or trifluoromethyl; and wherein $Y^1$ comprises a tri-substituted aryl group; wherein the alkyne handles are adapted to cross-link to an azide handle of a linking component via click chemistry (e.g., copper click chemistry). In some embodiments, the triazabutadiene comprises is linked to a peptide, an oligonucleotide, or a drug. In some embodiments, the linking component with the azide handle comprises a peptide, an oligonucleotide, or a drug.

The present invention also feature a method of detecting an interaction between a first component and a second component, said method comprising cleaving a triazabutadiene linked to the first component via a first triazole formed from click chemistry and to the second component via a second triazole formed from click chemistry, wherein cleaving the triazabutadiene liberates a diazonium species whereupon the diazonium species reacts with an electron-rich phenyl system to form a detectable signal, said detectable signal being indicative of interaction between the first component and the second component. In some embodiments, the triazabutadiene is according to Formula C, wherein both $X^1$ and $X^2$ comprised a terminal alkyne handle prior to formation of the first triazole and second triazole via click chemistry.

The present invention also features a method of linking a functional group or component to a clickable triazabutadiene, said functional group or component comprising an azide handle, said clickable triazabutadiene being according to (a) Formula B wherein $X^1$ comprises a terminal alkyne handle; or (b) Formula C wherein either $X^1$ comprises a terminal alkyne, $X^2$ comprises a terminal alkyne handle, or both $X^1$ and $X^2$ comprise a terminal alkyne handle; wherein A=S, O, or N; D=H, —CH=CH—CH=E-, halides, cyano, sulfonates, alkyl chain, or trifluoromethyl; E=H, —CH=CH—CH=D-, halides, cyano, sulfonates, alkyl chain, or trifluoromethyl; and wherein $Y^1$ comprises a tri-substituted aryl group; said method comprising subjecting the clickable triazabutadiene and functional group or component to copper click chemistry, wherein copper click chemistry links the clickable triazabutadiene and functional group or component via formation of a triazole from the alkyne handle and the azide handle. In some embodiments, the functional group comprises a water solubility functional group.

In some embodiments, the component comprises a peptide, an oligonucleotide, or a drug.

In some embodiments, the clickable triazabutadiene is according to Formula C wherein both $X^1$ and $X^2$ comprise a terminal alkyne handle; wherein A=S, O, or N; D=H, —CH=CH—CH=E-, halides, cyano, sulfonates, alkyl chain, or trifluoromethyl; E=H, —CH=CH—CH=D-, halides, cyano, sulfonates, alkyl chain, or trifluoromethyl; and wherein $Y^1$ comprises a tri-substituted aryl group. The alkyne handle of $X^1$ is adapted to cross-link to an azide handle of a first linking component via click chemistry, and the alkyne handle of $X^2$ is adapted to cross-link to an azide handle of a second component via click chemistry. In some embodiments, the first linking component comprises a biological component and the second linking component comprises a functional group conferring water-solubility. In some embodiments, both the first linking component and the second linking component comprise a biological component. In some embodiments, the tri-substituted aryl group of $Y^1$ comprises mesityl, a NHS-ester moiety, an oligonucleotide, a peptide; a fluorescence quencher; a pro-fluorophore; an alkyne; a triazene; an aldehyde; an amine; an aminooxy;

a halogen; or a combination thereof. In some embodiments, the biological component comprises a peptide, an oligonucleotide, or a drug.

In some embodiments, the clickable triazabutadiene is according to Formula C wherein both $X^1$ and $X^2$ comprise a terminal alkyne handle, wherein the alkyne handle of $X^1$ is adapted to cross-link to an azide handle of a first linking component via click chemistry, and the alkyne handle of $X^2$ is adapted to cross-link to an azide handle of a second component via click chemistry. In some embodiments, A=S, O, or N; D=H, —CH=CH—CH=E-, halides, cyano, sulfonates, alkyl chain, or trifluoromethyl; E=H, —CH=CH—CH=D-, halides, cyano, sulfonates, alkyl chain, or trifluoromethyl; and $Y^1$ comprises a tri-substituted aryl group. In some embodiments, the tri-substituted aryl group of $Y^1$ comprises mesityl, a NHS-ester moiety, an oligonucleotide, a peptide; a fluorescence quencher; a profluorophore; an alkyne; a triazene; an aldehyde; an amine; an aminooxy; a halogen; or a combination thereof. In some embodiments, the first linking component comprises a biological component and the second linking component comprises a functional group conferring water-solubility. In some embodiments, the biological component comprises a peptide, an oligonucleotide, or a drug.

In some embodiments, the clickable triazabutadienes of the present invention are according to (a) Formula B wherein $X^1$ comprises a terminal azide handle; or (b) Formula C wherein either $X^1$ comprises a terminal azide, $X^2$ comprises a terminal azide handle, or both $X^1$ and $X^2$ comprise a terminal azide handle; wherein A=S, O, or N; D=H, —CH=CH—CH=E-, halides, cyano, sulfonates, alkyl chain, or trifluoromethyl; E=H, —CH=CH—CH=D-, halides, cyano, sulfonates, alkyl chain, or trifluoromethyl; and wherein $Y^1$ comprises a tri-substituted aryl group; wherein the azide handles are adapted to cross-link to an alkyne handle of a linking component via click chemistry.

In some embodiments, the clickable triazabutadienes of the present invention are according to (a) Formula B wherein $X^1$ comprises a terminal azide handle or a terminal alkyne handle; or (b) Formula C wherein either $X^1$ comprises a terminal azide handle or a terminal alkyne handle, $X^2$ comprises a terminal azide handle or a terminal alkyne handle, or both $X^1$ and $X^2$ comprise a terminal azide handle or a terminal alkyne handle; wherein A=S, O, or N; D=H, —CH=CH—CH=E-, halides, cyano, sulfonates, alkyl chain, or trifluoromethyl; E=H, —CH=CH—CH=D-, halides, cyano, sulfonates, alkyl chain, or trifluoromethyl; and wherein $Y^1$ comprises a tri-substituted aryl group; wherein azide handles are adapted to cross-link to an alkyne handle of a linking component via click chemistry or alkyne handles are adapted to cross-link to an azide handle of a linking component via click chemistry.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

DETAILED DESCRIPTION OF THE INVENTION

I. Triazabutadiene Molecules

Figure 1:
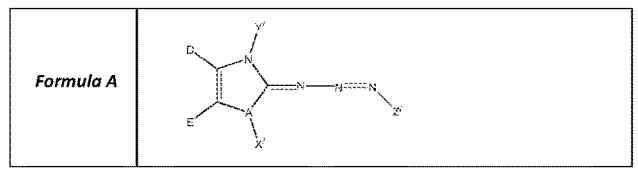
FIG. 1 shows non-limiting examples of triazabutadiene molecules.
Figure 1:
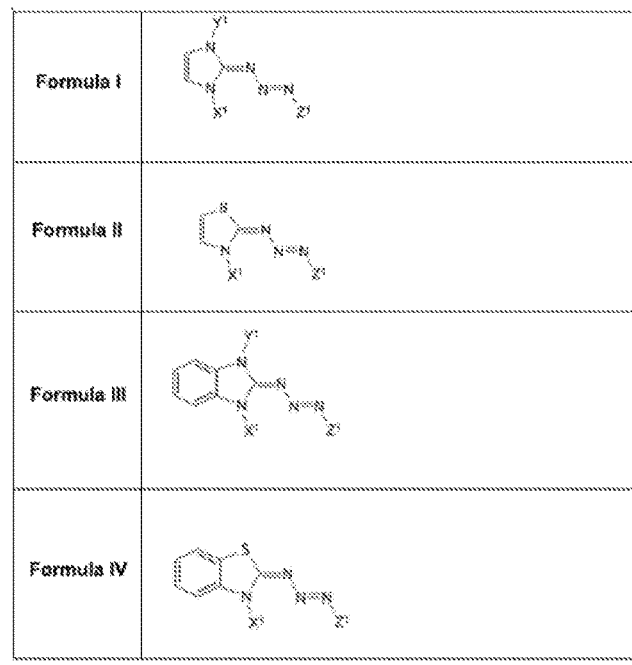

The present invention features triazabutadiene molecules. Non-limiting examples of formulas for triazabutadiene molecules of the present invention are of shown in FIG. 1. For example, in some embodiments, triazabutadienes are according to Formula A. Examples of Formula A are shown as Formula I, II, III, and IV. The present invention is not limited to Formula A, Formula I, Formula II, Formula III, and Formula IV. Referring to FIG. 1, in some embodiments, A=S, O, or N. In some embodiments, D=H, —CH=CH—CH=E-, halides, cyano, sulfonates, alkyl chain, or trifluoromethyl. In some embodiments, E=H, —CH=CH—CH=D-, halides, cyano, sulfonates, alkyl chain, or trifluoromethyl.

In some embodiments, $X^1$ is a moiety conferring water solubility. In some embodiments, $Y^1$ is a tri-substituted aryl group. In some embodiments, the $Y^1$ (e.g., the tri-substituted aryl group) comprises a NHS-ester moiety (e.g., for protein linkage); an oligonucleotide; a peptide; a fluorescence quencher; a pro-fluorophore; an alkyne (e.g., for click chemistry); a triazene (e.g., from click reaction); the like, or a combination thereof. In some embodiments, $Y^1$ comprises an aldehyde; an amine (e.g., Fmoc protected), aminooxy, halogen (e.g., radio isotope); the like, or a combination thereof. In some embodiments, $Z^1$ is an optionally substituted aryl. In some embodiments, $Z^1$ comprises a NHS-ester moiety; an oligonucleotide; a peptide; a fluorescence quencher; a pro-fluorophore; a biologically active acid labile compound; a prodrug comprising a phenolic functional group; releasable cargo; an alkyne (e.g., for click chemistry); a triazene (e.g., from click reaction); a polymerization residue (e.g., epoxide, polystyrene, alpha-beta-unsaturated ester acrylate, polyacrylamide, an amine, etc.), the like, or a combination thereof. In some embodiments, $Z^1$ comprises an aldehyde; an amine (e.g., Fmoc protected), aminooxy, halogen (e.g., radio isotope); the like, or a combination thereof.

In some embodiments, $X^1$ may comprise a functional group that confers water solubility. In some embodiments, $X^1$ comprise a moiety of the formula —$R^1$-$Q^1$, wherein $R^1$ is $C_{1-6}$ alkylene, and $Q^1$ is sulfate, sulfonate, phosphate, a quaternary ammonium cation, or an alkyl, aryl or propargylic containing moiety that can facilitate coupling to other azides via [3+2] cycloaddition chemistry. In some embodiments, $X^1$ is a moiety of the formula —$R^1$-$Q^1$, wherein $R^1$ is an alkane, e.g., $C_{1-6}$ alkylene. In some embodiments, $Q^1$ is sulfate (e.g., —(O)$_n$SO$_3$R$^a$, where n is 0 or 1, and R$^a$ is C1-6 alkyl or typically H), phosphate (e.g., —(O)$_n$PO$_3$R$^a$, where n is 0 or 1, and R$^a$ is C1-6 alkyl or typically H), or a quaternary ammonium cation (e.g., —[NR$^a$R$^b$R$^c$]$^+$, where each of R$^a$, R$^b$, and R$^c$ is independently H or $C_{1-6}$ alkyl). As used herein, the term "alkyl" refers to a saturated linear monovalent hydrocarbon moiety of one to twelve, typically one to six, carbon atoms or a saturated branched monovalent hydrocarbon moiety of three to twelve, typically three to six, carbon atoms. Examples of alkyl groups include, but are not limited to, methyl, ethyl, n-propyl, 2-propyl, tert-butyl, pentyl, and the like. The term "alkylene" refers to a saturated linear divalent hydrocarbon moiety of one to twelve, typically one to six, carbon atoms or a branched saturated divalent hydrocarbon moiety of three to twelve, typically three to six, carbon atoms. Examples of alkylene groups include, but are not limited to, methylene, ethylene, propylene, butylene, pentylene, and the like.

Triazabutadiene molecules of the present invention are readily soluble in water. In some embodiments, the solubility of the triazabutadiene molecules in water is at least 23 g/L of water (50 mM). In some embodiments, the triazabutadiene molecules are stable in pH 7.4 phosphate buffer. The phosphate buffer solutions are commercially available or can be prepared, for example, as described in http://cshprotocols.cshlp.org/content/2006/1/pdb.rec8247. In some instances, the half-life of the triazabutadiene molecules of the present invention in pH 7.4 phosphate buffer solution is at least 24 hours.

Stability of the triazabutadiene molecule can be measured in various ways. In some embodiments, stability is measured by the half-life of the molecule (or the half-life of the molecule in a particular buffer at a particular pH). In some embodiments, the molecule has a half-life of at least 12 hours in a pH 7.4 buffer. In some embodiments, the molecule has half-life of at least 24 hours in a pH 7.4 buffer. In some embodiments, the molecule has half-life of at least 36 hours in a pH 7.4 buffer. In some embodiments, the triazabutadiene molecule has a half-life of at least 8 hours. In some embodiments, the triazabutadiene molecule has a half-life of at least 10 hours. In some embodiments, the triazabutadiene molecule has a half-life of at least 12 hours. In some embodiments, the triazabutadiene molecule has a half-life of at least 20 hours. In some embodiments, the triazabutadiene molecule has a half-life of at least 24 hours. In some embodiments, the triazabutadiene molecule has a half-life of at least 30 hours. In some embodiments, the triazabutadiene molecule has a half-life of at least 36 hours. The present invention is not limited to the aforementioned examples of stability measurements.

Without wishing to limit the present invention to any theory or mechanism, it is believed that the triazabutadiene molecules of the present invention are advantageous because the triazabutadiene molecules can be easily modified (e.g., various different functional groups can be easily used as $X^1$, $Y^1$, or $Z^1$ (see FIG. 1). And, the release of the diazonium species following triazabutadiene molecule breakdown (via certain mechanisms, as described below) provides a functional group that can be taken advantage of in various applications. Also, it may be considered advantageous that the breakdown of the triazabutadiene molecule is irreversible.

II. Cleavage of Triazabutadiene Molecules a. Water and/or Low pH

Figure 2A:
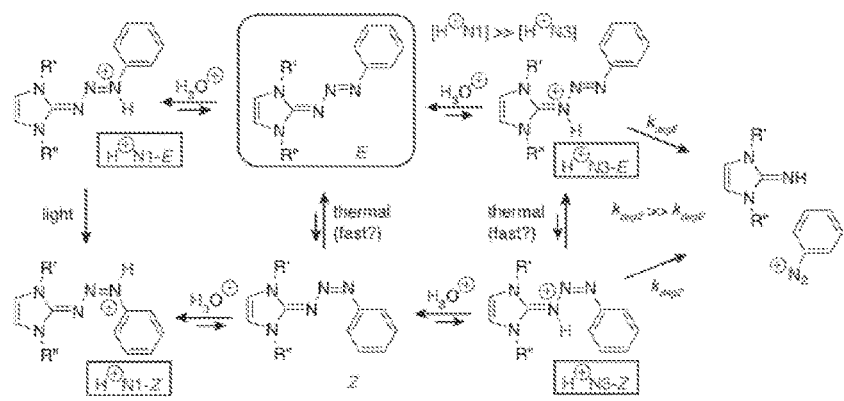
FIG. 2A shows triazabutadiene molecules undergoing decomposition to diazonium salts (and cyclic guanidine species). Note the reaction/equilibrium arrows are not to scale.

The present invention shows that triazabutadiene molecules may break down in the presence of water to generate reactive aryl diazonium compounds. For example, FIG. 2A shows that triazabutadiene molecules of the present invention can undergo decomposition to diazonium salts (reactive aryl diazonium compounds) and cyclic guanidine species. Aryl diazonium compounds can react with electron-rich aryl rings (e.g., aryl species wherein the bond of interest is a nitrogen-carbon bond; indoles, anilines, phenol-containing compounds such as resorcinol or tyrosine, etc.) to form stable azobenzene linkages (e.g., an aryl azo dye, e.g., Sudan Orange). (Note the present invention is not limited to the aforementioned phenol-containing species. In some embodiments, imidazole compounds (e.g., purine bases like guanine) may be used in lieu of a phenol-containing compound.) The diazonium species may not necessarily react with an electron-rich aryl rings compound (e.g., phenol species), for example if a phenol species is not present. The diazonium species may irreversibly extrude nitrogen gas to generate an aryl cation, which will rapidly be quenched by solvating water, thus synthesizing a new phenolic compound (e.g., HO-Ph, wherein Ph refers to the phenyl ring); thus, the diazonium portion of the triazabutadiene molecule may function as a masked hydroxyl group.

Figure 2B:
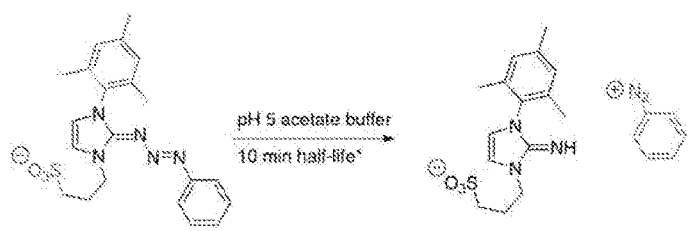
FIG. 2B shows a triazabutadiene molecule breaking down (in low pH conditions) to a diazonium species and a cyclic guanidine species.

In some embodiments, the triazabutadiene molecules are acid labile, e.g., unstable at particular pH levels (see FIG. 2B). For example, decreases in pH increase the rate at which the triazabutadiene molecules break down (the half life of the molecule decreases). In some embodiments, the triazabutadiene molecules are unstable at low (lowered) pH levels (e.g., lowered pH as compared to a particular pH that the molecule may be stored at, e.g., a pH wherein the molecule has a particular desired half life). Low pH levels, in some example, may be a sub-physiological pH (7.4 or less). In some embodiments, the triazabutadiene molecules are (more) unstable at pH 7.0 or less, pH 6.8 or less, pH 6.5 or less, pH 6.2 or less, pH 6.0 or less, pH 5.8 or less, pH 5.6 or less, pH 5.5 or less, pH 5.2 or less, pH 5.0 or less, etc.

The term "low pH" may refer to several different pH levels. Since the functional groups attached to the molecule (e.g., see $X^1$, $Y^1$, $Z^1$ of Formula I) affect the stability of the molecule (as well as water solubility), the pH that is necessary to increase the rate of breakdown of the triazabutadiene molecule (e.g., the "lowered pH") may be different for different molecules. In some embodiments, the low pH is a pH of 7.4 or less. In some embodiments, the low pH is a pH of 7.2 or less. In some embodiments, the low pH is a pH of 7.0 or less. In some embodiments, the low pH is a pH of 6.8 or less. In some embodiments, the low pH is a pH of 6.6 or less. In some embodiments, the low pH is a pH of 6.6 or less. In some embodiments, the low pH is a pH of 6.6 or less. In some embodiments, the low pH is a pH of 6.5 or less. In some embodiments, the low pH is a pH of 6.4 or less. In some embodiments, the low pH is a pH of 6.2 or less. In some embodiments, the low pH is a pH of 6.0 or less. In some embodiments, the low pH is a pH of 5.8 or less. In some embodiments, the low pH is a pH of 5.5 or less. In some embodiments, the low pH is a pH of 5.0 or less.

In some embodiments, the triazabutadiene molecules can break down without the presence of the low pH (the molecules have half lives); however, in some embodiments, a lowered pH enhances the reaction (e.g., increases the rate of reaction). As such, a low pH may or may not be used with the molecules and/or methods of the present invention. In some embodiments, the triazabutadiene molecule has a half-life of no more than 1 hour in a pH 7.4 aqueous solution. In some embodiments, the triazabutadiene molecule has a half-life of no more than 30 minutes in a pH 7.4 aqueous solution. In some embodiments, the triazabutadiene molecule has a half-life of no more than 15 minutes in a pH 7.4 aqueous solution.

The present invention also features methods of breaking down triazabutadiene molecules. In some embodiments, the method comprises subjecting the molecule to water. In some embodiments, the method comprises subjecting the molecule to a low pH (e.g., a low pH that is appropriate for the molecule, e.g., a lowered pH that increases the rate at which the triazabutadiene molecule breaks down).

In some embodiments, the reaction of the triazabutadiene molecule to the diazonium species occurs in water within 10 seconds minutes. In some embodiments, the reaction of the triazabutadiene molecule to the diazonium species occurs in water within 30 seconds minutes. In some embodiments, the reaction of the triazabutadiene molecule to the diazonium species occurs in water within 1 minute. In some embodiments, the reaction of the triazabutadiene molecule to the diazonium species occurs in water within 5 minutes. In some embodiments, the reaction of the triazabutadiene molecule to the diazonium species occurs in water within 10 minutes. In some embodiments, the reaction of the triazabutadiene molecule to the diazonium species occurs in water within 15 minutes. In some embodiments, the reaction of the triazabutadiene molecule to the diazonium species occurs in water within 20 minutes. In some embodiments, the reaction of the triazabutadiene molecule to the diazonium species occurs in water within 25 minutes. In some embodiments, the reaction of the triazabutadiene molecule to the diazonium species occurs in water within 30 minutes. In some embodiments, the reaction of the triazabutadiene molecule to the diazonium species occurs in water within 45 minutes. In some embodiments, the reaction of the triazabutadiene molecule to the diazonium species occurs in water within 60 minutes.

In some embodiments, the diazonium species may be visually differentiated from the triazabutadiene species, e.g., the diazonium species is visually distinct (e.g., a different color) from the triazabutadiene molecule. If applicable, in some embodiments, the aryl azo dye may be visually differentiated from the triazabutadiene species and the diazonium species, e.g., the aryl azo dye is visually distinct (e.g., a different color) from the triazabutadiene species and the diazonium species.

Given the possibility that the aryl azo dye is visually distinct from the triazabutadiene molecule (and/or the diazonium species), the present invention also features methods of producing a visually detectable molecule. In some embodiments, the method comprises providing a triazabutadiene molecule according to the present invention and subjecting the triazabutadiene molecule to water and/or a low pH (or light as discussed below, or light and low pH, etc.). The low pH (or light, or light and low pH, etc.) initiates (e.g., increases the rate of) the irreversible reaction to produce the diazonium species and the cyclic guanidine species. As previously discussed, the diazonium species may be visually distinct from the triazabutadiene molecule; therefore the reaction produces a visually detectable molecule.

b. Reductive Cleavage

Other mechanisms may be used to break down triazabutadiene molecules of the present invention. For example, in some embodiments, reducing conditions increase the rate at which the triazabutadiene molecules break down. Thus, the present invention also features methods of reductive cleavage of triazabutadiene molecules. For example, triazabutadiene molecules (e.g., triazabutadiene scaffolds) may be readily cleaved using reducing agents such as but not limited to sodium dithionite (sodium hydrosulfite) ($Na_2S_2O_4$). In some embodiments, the reducing agent comprises lithium aluminum hydride, sodium borohydride, or the like. In some embodiments, electrochemical reduction may be used in accordance with the present invention. Reductive cleavage of the triazabutadiene molecules provides a urea functionality and a terminal aryl triazene. In some embodiments, the aryl triazene is further reduced in the presence of excess reducing agent (e.g., sodium dithionite). In some embodiments, the reduction can be observed visually by the change in color of a solution. For example, there may be a subtle change of yellows that results from a loss of a shoulder in UV/vis spectrum.

In some embodiments, the ratio of the concentration of the triazabutadiene to the reducing agent is about 1:1. In some embodiments, the ratio of the concentration of the triazabutadiene to the reducing agent is about 1:2. The present invention is not limited to the aforementioned ratios. For example, in some embodiments, the ratio of the concentration of the triazabutadiene to the reducing agent is about 2:3, 4:5, etc. The present invention is not limited to the aforementioned ratio of concentrations.

In some embodiments, the reduction can occur within about 10 minutes, within about 15 minutes, within about 20 minutes, within about 25 min, within about 30 min, etc., at room temperature. Without wishing to limit the present invention to any theory or mechanism, it is believed that reductive cleavage of the triazabutadiene molecules is advantageous because it can occur rapidly (e.g., within 10 minutes, within 15 minutes). Also, the triazabutadiene molecules that are highly stable in acid (e.g., a p-CN derived triazabutadiene) may still be susceptible to reducing conditions.

In some embodiments, reductive cleavage of triazabutadiene molecules may also be used to cleave unreacted triazabutadienes that did not undergo diazonium formation/ reaction chemistry that is associated with a drop in pH (or other mechanism) as described above (a sort of quench for the pH chemistry).

c. Light-Initiated Cleavage

In some embodiments, light increases the rate at which the triazabutadiene molecule breaks down (into the cyclic guanidine species and the diazonium species). The present invention features triazabutadienes that, upon photo-irradiation, may be rendered more basic in a reversible fashion. A protecting group of a masked base may decompose to reveal a basic nitrogen atom upon exposure to light. Or, a basic nitrogen atom of a molecule obscured by a steric wall may be reversibly swung away in a photochemically-triggered manner. The present invention shows the intrinsic basicity of a nitrogen-containing functional group may be altered by a photochemical event.

Methods of breaking down triazabutadiene molecules may feature subjecting the molecule to light. The light may, for example, include wavelengths of about 400 nm. The present invention is not limited to wavelengths of 400 nm or about 400 nm. For example, in some embodiments, the wavelength is from 350 nm to 400 nm (e.g., 370 nm). In some embodiments, the wavelength is from 360 nm to 410 nm. In some embodiments, the wavelength is from 330 nm to 420 nm. In some embodiments, the wavelength is from 340 nm to 430 nm. In some embodiments, the method comprises subjecting the molecule to a low pH and to light.

As previously discussed, light-promoted reactivity and light-facilitating E/Z isomerization has been observed. In some embodiments, a system such as a UV-LED pen may be used for these reactions, however the present invention is not limited to a UV-LED pen and may utilize any appropriate system. The UV-LED pens may allow for relatively narrow bandwidth irradiation of these compounds (but are not limited to these bandwidths). The color of the bulk material shifts as a result of electronic perturbations to the aryl azide starting material. These experiments may be performed in basic aqueous solutions to maintain the solvation properties of water while also preventing the degradation pathway stemming from protonation. These experiments are not limited to basic aqueous solutions. Without wishing to limit the present invention to any theory or mechanism, it may be considered advantageous that the breakdown of the triazabutadiene molecule is irreversible.

III. Synthesis of Water-Soluble Triazabutadiene Molecules and Experimental Examples Synthesis of 1-mesityl-1-H-imidazole: To a solution of 2,4,6-trimethylaniline (1.35 g, 10.0 mmol) in methanol (15 mL) was added a solution of glyoxal (40%) (1.14 mL, 40% in water, 10. mmol). The mixture was stirred at room temperature until a solid formed. Thereafter, solid ammonium chloride (1.07 g, 20 mmol), formaldehyde (37%) (1.6 mL 37% in water, 60. mmol) and methanol (40 mL) were added, and the mixture was heated to reflux for one hour. After the hour, phosphoric acid (1.4 ml of an 85% solution) was added drop wise and the mixture was refluxed for an additional eight hours. Upon cooling to room temperature ice (30 g) was added and the solution was brought to a pH of 9 with potassium hydroxide (40% in water). The following mixture was extracted repeatedly with diethyl ether. The ether phase was dried over magnesium sulfate and solvent removed in vacuo to form a brown solid which was filtered and washed with hexanes to give the product (0.785 g; 42%). 1H NMR (500 MHz, CDCl$_3$): δ 7.45 (t, J=1.1 Hz, 1H), 7.25 (t, J=1.1 Hz, 1H), 6.99 (dp, J=1.3, 0.7 Hz, 2H), 6.91 (t, J=1.3 Hz, 1H), 2.36 (t, J=0.7 Hz, 3H), 2.01 (t, J=0.6 Hz, 6H). 13C NMR (126 MHz, CDCl3) δ 138.80, 137.47, 135.42, 133.40, 129.55, 128.96, 120.02, 21.03, 17.33. (see Liu, J. et al. Synthesis 2003, 17, 2661-2666).

Synthesis of 3-(1-mesityl-1H-imidazol-3-ium-3-yl) propane-1-sulfonate: To a solution of 1-mesityl-1-H-imidazole (1.00 g, 5.36 mmol) in toluene (30 mL) was added 1,3-propanesultone (1.00 g, 8.18 mmol) and the mixture was heated to reflux overnight. The mixture was allowed to cool to room temperature and the off-white precipitate collected by filtration. The precipitate was further washed with diethyl ether and dried using a vacuum oven to yield a solid (1.40 g; 84%). 1H NMR (500 MHz, D2O): δ 8.92 (t, J=1.6 Hz, 1H), 7.75 (t, J=1.8 Hz, 1H), 7.49 (t, J=1.8 Hz, 1H), 7.06 (q, J=0.8 Hz, 2H), 4.44 (t, J=7.1 Hz, 2H), 2.39-2.31 (m, 2H), 2.25 (s, 3H), 1.96 (s, 6H). 13C NMR (126 MHz, D2O) δ 141.42, 136.54, 134.64, 130.74, 124.34, 123.00, 48.18, 47.17, 25.03, 20.17, 16.29.

Synthesis of Potassium 3-(3-mesityl-2-(phenyltriaz-2-en-1-ylidene)-2, 3-dihydro-1H-imidazol-1-yl) propane-1-sulfonate: To a slurry of 3-(1-mesityl-1H-imidazol-3-ium-3-yl)propane-1-sulfonate (50 mg, 0.16 mmol) in dry THF (6 mL), was added a solution of phenyl azide in THE (0.16 mL, 1 M, 0.16 mmol). To the solution was added KO-t-Bu (24 mg, 0.21 mmol) in one portion and the resulting mixture was stirred under argon for 4 hours. Hexanes (1 mL) was then added and the reaction mixture was filtered. The solvent was removed and the residue taken up in a minimal amount of DCM and on trituration with hexanes, pure product was obtained by filtration as a yellow powder (61 mg, 81%). 1H NMR (500 MHz, DMSO-d6) δ 7.32 (d, J=2.4 Hz, 1H), 7.07-7.02 (m, 4H), 6.99-6.94 (m, 1H), 6.84 (d, J=2.4 Hz, 1H), 6.51-6.47 (m, 2H), 4.09 (t, J=7.1 Hz, 2H), 2.34 (s, 3H), 2.12-2.04 (m, 2H), 1.95 (s, 6H). 13C NMR (126 MHz, DMSO-d6) δ 152.19, 151.13, 137.94, 136.15, 134.31, 129.31, 128.60, 125.26, 120.90, 117.61, 117.24, 48.52, 45.05, 25.80, 21.06, 17.95. Using the procedures described herein, the p-methoxy and p-nitro analogs (from the p-MeO aryl azide and p-NO2 aryl azide) were also prepared.

For decomposition experiments, buffers were made to the appropriate pH in a 9:1 mix of H2O:D2O. These solutions were added to the compound being assayed such that the buffer capacity was at least 10 fold the concentration of the compound. Some experiments used 5 mg compound in 0.5 mL of buffer. These were immediately inserted into an NMR instrument and scans were taken at even time intervals to calculate the half-life of the compound based on integration.

As another non-limiting example, an azide (e.g., NHS-azide) to N-heterocyclic carbene (NHC) route may be used to synthesize triazabutadiene molecules.

IV. Applications and Methods of Use of Triazabutadienes

The triazabutadiene molecules of the present invention may be utilized for a variety of purposes. For example, in some embodiments, the triazabutadiene molecules of the present invention are utilized for a cleavable linkage (e.g., chemoselectively-cleavable linkage) for use in biological/complex settings where rapid, clean cleavage is of interest. In some embodiments, the triazabutadiene molecules are used for systems including but not limited to drug delivery systems, protein-protein interaction systems, pH environment detection systems, etc. Applications of these triazabutadienes may fall under one (or more) categories of reactivity.

a. Diazonium Coupling Applications and Triazabutadiene Probes

Regarding diazonium coupling, the triazabutadiene molecules may be used for applications involving pH-dependent protein coupling. General examples involve methods for detecting protein-protein proximity or protein-protein interactions (in a sample). In some embodiments, the method comprises providing a first protein, wherein the first protein is conjugated with a triazabutadiene molecule according to the present invention. The first protein may be introduced to a sample. In some embodiments, the triazabutadiene molecule encounters a low pH in the sample; in some embodiments, acid is added to the sample to lower the pH appropriately. As previously discussed, in the low pH environment, the triazabutadiene molecule undergoes the irreversible reaction yielding the diazonium species and the cyclic guanidine species. As previously discussed, the diazonium species is adapted to react with a phenol group; thus if there is a nearby protein with a tyrosine residue, the diazonium species may react with it yielding an azobenzene product (often colored, for example the dye, Sudan Orange G is an azobenzene containing dye) that is visually distinct from the triazabutadiene molecule and the diazonium species. As such, detection of the azo dye may be indicative of proximity or interaction of the first protein and the second protein. Thus, in some embodiments, the method comprises adding a second protein to the sample, wherein a tyrosine of the second protein may react with the diazonium species. In some embodiments, the second protein is already in the sample. In some embodiments, a tyrosine or phenol species conjugated to the second protein. In some embodiments, the method comprises introducing to the sample a first antibody specific for a first protein, wherein the first antibody is conjugated with a triazabutadiene molecule according to the present invention. In some embodiments, the method comprises introducing to the sample a second antibody specific for a second protein. In some embodiments, the second antibody comprises a tyrosine. In some embodiments, the second antibody is conjugated with a phenol species. In some embodiments, the method comprises introducing an acid to the sample to appropriately lower the pH of the sample. As previously discussed, in the low pH environment, the triazabutadiene molecule undergoes the irreversible reaction yielding the diazonium species and the cyclic guanidine species. As previously discussed, the diazonium species is adapted to react with a phenol group; thus if the phenol species is nearby, the diazonium species may react with it yielding an azo dye that is visually distinct from the triazabutadiene molecule and the diazonium species. As such, detection of the azo dye may be indicative of proximity or interaction of the first protein and the second protein.

As a more specific example, the acid-labile reactivity of triazabutadienes may be used to assist in work deducing interaction partners between a virus and endosomally localized host proteins. Upon endosomal acidification a viral-bound diazonium species may be unmasked and this may go on to react with Tyr-containing proteins that are associating with the virus. It is possible that this system could be used to detect or trap an interaction that is relevant at a key point of viral entry, e.g., the fusion of membranes. Herein are non-limiting examples of synthesis of compounds that may be used in such systems, e.g., for modifying the viral surface. Lysine-reactive probes may be used to modify the surface of proteins. As previously discussed, a triazabutadiene molecule may be attached to a viral protein (e.g., a purified viral protein). Then, a system such as a cell line (e.g., mosquito cell line, human cell line, or even mosquitos themselves) may be infected with the viral protein. The infected system can be treated appropriately. The azo dye (e.g., Sudan Orange) may "label" any proteins that interact with or are nearby the viral protein (in the low pH environment). The present invention is not limited to this example. Lys-NHS conjugation chemistry may work well on the basic side of neutral, which may be beneficial for pH sensitive probes.

As previously discussed, the present invention features triazabutadienes that function as cross-linkers, e.g., cleavable cross-linkers. In some embodiments, the triazabutadiene cross-linkers allow for linking components via click chemistry, e.g., via copper-catalyzed azide-alkyne cycloadditions. For example, if a clickable handle (e.g., a terminal alkyne handle) is disposed on the triazabutadiene, it can be used to undergo 1,3-dipolar cycloaddition with an azide handle on a different component (e.g., to yield a 1,4-disubstituted triazole).

The use of triazabutadienes and click chemistry allows for the linking of a wide range of compounds for either chemical or biological applications. Note that in general, in order for the azide-alkyne cycloaddition to occur, it must be activated with a Cu(I) source. In some embodiments, the Cu(I) initiator can come from copper-halide reagents or Cu(II) sources that are reduced in situ. Cu(II) salts such as $CuSO_4$ allow click chemistry to proceed in aqueous conditions with mild reducing agents such as sodium ascorbate. Cu(I) halide salts generally require a base/ligand to coordinate the metal insertion and prevent oxidation. Without wishing to limit the present invention to any theory or mechanism, it is believed that copper click chemistry is versatile as it can be performed in a wide range of conditions. This may allow for tunability when it comes to finding the appropriate conditions for triazabutadiene functionalization.

Note that in some embodiments, the alkyne handle is disposed on the triazabutadiene and said alkyne handle can react with an azide handle on a different component. The present invention is not limited to the alkyne handle being deposed on the triazabutadiene. In some embodiments, the azide handle is disposed on the triazabutadiene and said azide handle can react with an alkyne handle on a different component. In some embodiments, both an alkyne handle and an azide handle is linked to the triazabutadiene.

Figure 3A:
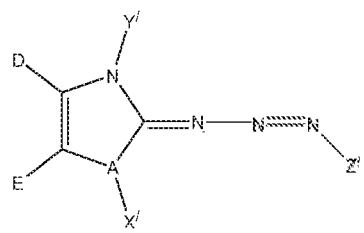
FIG. 3A shows examples of structures of triazabutadienes adapted for click chemistry (see Formula B and Formula C compared to Formula A).
Figure 3A:
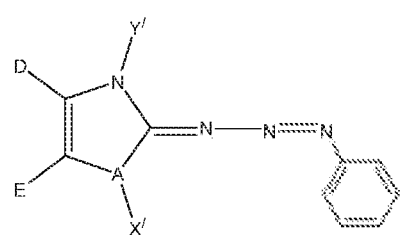
Figure 3A:
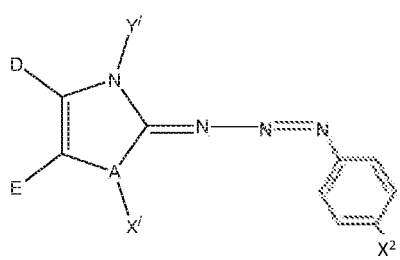

FIG. 3A shows non-limiting examples of structures of triazabutadienes adapted for click chemistry, e.g., Formula B and Formula C. In some embodiments, $X^1$ comprises an alkyne handle. In some embodiments, $X^2$ comprises an alkyne handle. In some embodiments, $X^1$ comprises an azide handle. In some embodiments, $X^2$ comprises an azide handle. In some embodiments, the clickable triazabutadiene is according to Formula B, wherein $X^1$ comprises a terminal alkyne handle. In some embodiments, the triazabutadiene is according to Formula C wherein $X^1$ comprises a terminal alkyne. In some embodiments, the triazabutadiene is according to Formula C wherein $X^2$ comprises a terminal alkyne handle. In some embodiments, the triazabutadiene is according to Formula C wherein both $X^1$ and $X^2$ comprise a terminal alkyne handle. In some embodiments, A=S, O, or N; D=H, —CH=CH—CH=E-, halides, cyano, sulfonates, alkyl chain, or trifluoromethyl. In some embodiments, E=H, —CH=CH—CH=D-, halides, cyano, sulfonates, alkyl chain, or trifluoromethyl. Note in some embodiments, the $X^1$ and $Y^1$ may be switched. For example, in some embodiments, A is sulfur, and the alkyne is branched off of the other nitrogen.

Figure 3B:
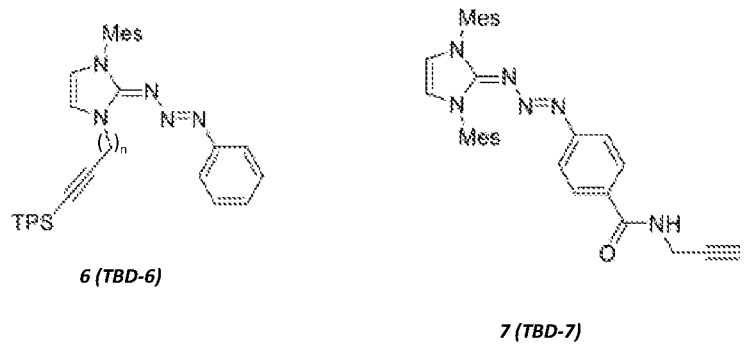
FIG. 3B shows non-limiting examples of triazabutadienes adapted for click chemistry, e.g., triazabutadienes comprising alkyne handles.

As previously discussed, in some embodiments, the triazabutadiene comprises an alkyne handle. FIG. 3B shows TBD-6 and TBD-7, two non-limiting examples of triazabutadienes with alkyne handles. In some embodiments, the alkyne handle is linked to the imidazole portion of the triazabutadiene (TBD-6). In some embodiments the, the alkyne handle is linked to the aryl portion of the triazabutadiene (TBD-7). Note in some embodiments, the alkyne handle comprises a protection group (TBD-6 comprises a protection group). In some embodiments, the protection group comprises chlorotripropylsilane (TPS); however, the protection group is not limited to TPS. For example, in some embodiments, the protection group comprises chlorotrimethylsilane (TMS-Cl), chlorotriethylsilane (TES-Cl), etc.

Figure 4A:
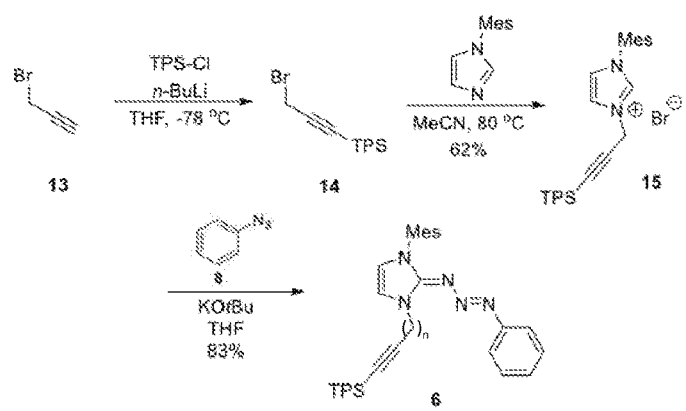
FIG. 4A shows synthesis of a triazabutadiene (TBD-6) comprising a terminal alkyne handle on the imidazole portion of the triazabutadiene. Note in some embodiments, n=1, n=2, n=3, n=4, etc.
Figure 4B:
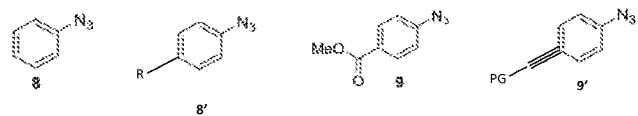
FIG. 4B shows examples of azides for clickable triazabutadiene synthesis, e.g., synthesis of a triazabutadiene such as TBD-6 of FIG. 4A. Note in azide 9', PG stands for protecting group.

The synthesis of TBD-6 (from FIG. 3B) was performed as shown in FIG. 4A beginning with silylation of propargyl bromide (Compound 13). (Protection of the alkyne was necessary due to the similar $pK_a$ values of an alkyne ($pK_a$=25) and the proton on a NHC-salt ($pK_a$=21-24)). Propargyl bromide (Compound 13) was treated with n-butyllithium (n-BuLi) to deprotonate the terminal alkyne to render it nucleophillic so it would react with Chlorotripropylsilane (TPS-Cl) yielding the silyl-protected alkyne (Compound 14). The crude of Compound 14 was only partially purified by flash column chromatography, and was taken to reflux with N-mesitylimidazole in acetonitrile for 2 days to produce the imidazolium salt Compound 15. The coupling of Compound 15 and phenyl azide Compound 8 took place in dry THF. KOtBu was added to generate the NHC to react with the azide and form Compound 6 in moderate yield. This reaction was very moisture sensitive and acquiring best yield in dry conditions. The present invention is not limited to phenyl azide (Compound 8 of FIG. 4A and FIG. 4B). In some embodiments, synthesis of clickable triazabutadienes features alternative azide compounds such as Compound 8' (e.g., Compound) (see FIG. 4B). Note that the methods of using a clickable triazabutadiene according to TBD-6 for click chemistry comprises removing of the protection group (e.g., deprotecting the silyl group). In some embodiments, the use of a compound such as but not limited to tetra-n-butylammonium fluoride (TBAF) in the reaction may allow for deprotecting the silyl group to allow a click reaction to proceed.

Figure 4C:
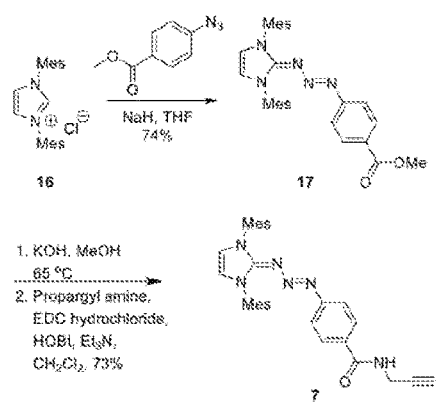
FIG. 4C shows synthesis of a triazabutadiene (TBD-7) comprising an alkyne handle on the aryl portion of the triazabutadiene.

The synthesis of TBD-7 (from FIG. 3B) was performed as shown in FIG. 4C. Bis-mesitylimidazolium chloride salt Compound 16 was deprotonated with sodium hydride (NaH) to generate the reactive NHC species in the presence of p-azido-methylbenzoate Compound 9 to form Compound 17. The K-salt intermediate of Compound 7 underwent 1-Ethyl-3-(3-dimethylaminopropyl)carbodiimide (EDC) coupling with hydroxybenzothiazole (HOBt) in order to form a reactive HOBt ester intermediate. This rendered the carbonyl group highly electrophilic for a nucleophilic attack by propargyl amine to produce the amide bond and the triazabutadiene Compound 7 with a terminal alkyne for click chemistry.

Figure 4D:
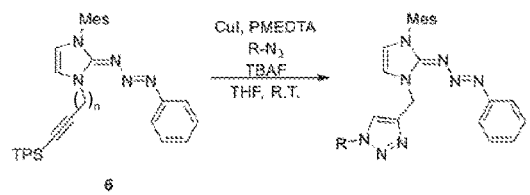
FIG. 4D shows click chemistry with a clickable triazabutadiene (TBD-6). Note in some embodiments, n=1, n=2, n=3, n=4, etc.

FIG. 4D shows click chemistry using a clickable triazabutadiene comprising an alkyne handle (TBD-6). Table 1 below shows examples of R groups attached to the azide handle that is clicked to the clickable triazabutadiene. The triazabutadiene 6, organic azide, CuI, and PMEDTA were in a solution of tetrahydrofuran (THF).

TABLE 1

Synthesis of imidazolium-substituted triazole-triazabutadiene

| Entry | R | Product | Time (hr) | Yield (%) |
|---|---|---|---|---|
| 1 | 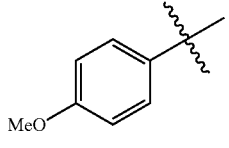 | 19 | 5 | 56 |

TABLE 1-continued

Synthesis of imidazolium-substituted triazole-triazabutadiene

| Entry | R | Product | Time (hr) | Yield (%) |
|---|---|---|---|---|
| 2 | 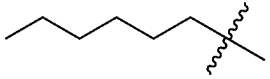 | 20 | 2 | 48 |

Figure 4E:
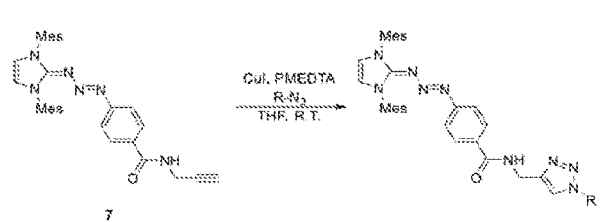
FIG. 4E shows click chemistry with a clickable triazabutadiene (TBD-7).

FIG. 4E shows click chemistry using a clickable triazabutadiene comprising an alkyne handle (TBD-7). Triazabutadiene Compound 7 (TBD-7) was subjected to similar conditions using the same azides (Table 2 below) with a minor alteration. Due to the installation of the alkyne handle after triazabutadiene synthesis, a protection step was unnecessary. The Cu-click reaction proceeded with moderate yields.

TABLE 2

Synthesis of aryl-substituted triazole-triazabutadiene

| Entry | R | Product | Time (hr) | Yield (%) |
|---|---|---|---|---|
| 1 | 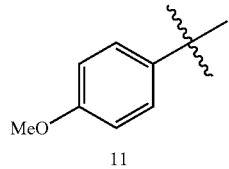 [SMILES: *c1ccc(OC)cc1] | 21 | 4 | 50 |
| 2 | 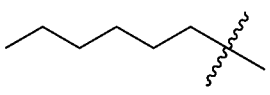 | 22 | 6 | 73 |

The present invention also features methods of cleaving said triazabutadienes, e.g., cleaving the clickable triazabutadienes that has undergone click chemistry and is in the cross-linking state, e.g., compounds such as the products of the reactions in FIG. 4D and FIG. 4E. In some embodiments, cleavage of the cross-linking triazabutadiene liberates the diazonium species; thus, the present invention also features methods that feature diazonium reactions following cleavage of said linking triazabutadienes.

Figure 5A:
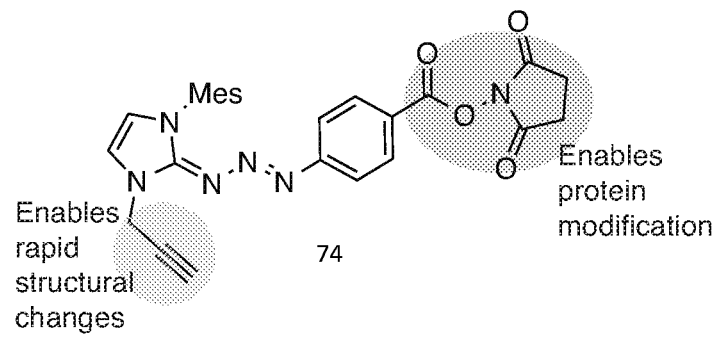
FIG. 5A shows a proposed lysine reactive triazabutadiene that can be rapidly modified in situ by click chemistry.
Figure 5B:
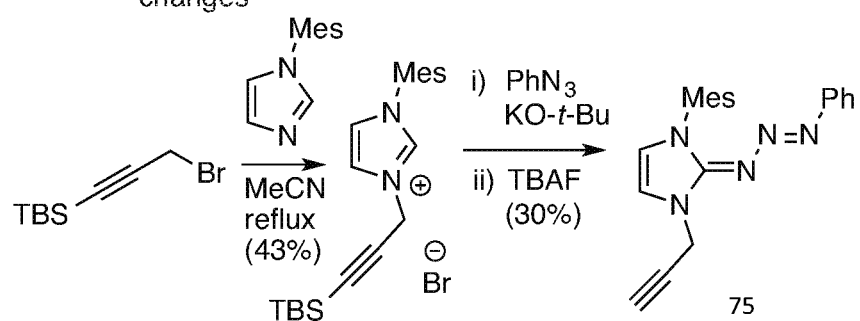
FIG. 5B shows preliminary synthesis of an alkyne containing triazabutadiene Compound 75.

To assess the role of charges and perturbations that the probes have on proteins alkyne-containing triazabutadiene Compound 74 may be synthesized (see FIG. 5A). The alkyne may allow further modification of the scaffold either pre or post protein modification. The proof of concept version of this probe was shown to undergo a Cu(I) catalyzed click reaction with p-azidotrifluoromethylbenzene (FIG. 5B).

Figure 5C:
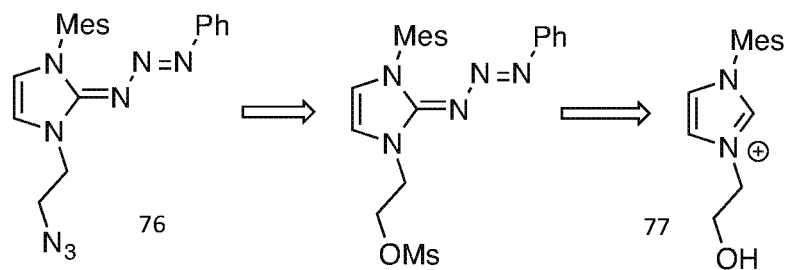
FIG. 5C shows proposed retrosynthesis of azide-containing triazabutadiene Compound 76 from imidazolium Compound 77.
Figure 5D:
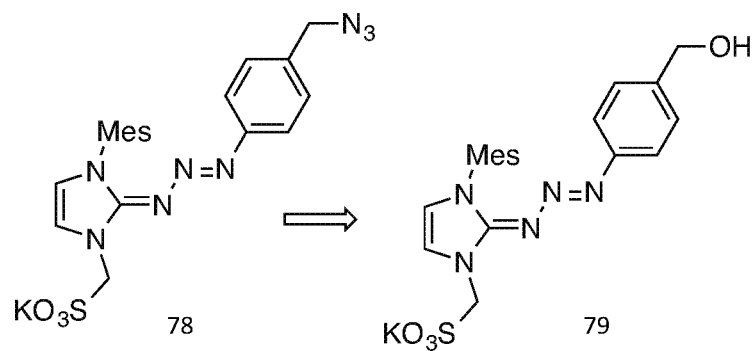
FIG. 5D shows benzylic azide Compound 78 can be made from previously synthesized alcohol Compound 79.

The azide version, Compound 76, may help remove the limits on coupling partners (FIG. 5C). To further expand coupling capabilities, an azide or alkyne on the aryl side of the triazabutadiene, like in Compound 78 (FIG. 5D), may allow for conjugation to alkyne- or azide-modified (respectively) unnatural amino acids, glycans, or other metabolites that are to be studied.

In the absence of a protein cross-linking event, there may be an aryl diazonium, which decomposes to a phenol and remains bound to the lysine. This phenol is likely prone to redox chemistry and as such represents an avenue for complexity during proteomic analysis. A self-immolating triazabutadiene has been designed to circumvent these pitfalls.

d. Diazonium Degradation for Cargo or Drug Release

In some embodiments, the triazabutadiene molecules of the present invention may be used in applications involving diazonium degradation to release cargo or drugs. For example, a group of applications takes advantage of the solvolysis of diazonium salts to produce phenolic byproducts. The degradation of diazonium salts to phenols, via aryl cations, is a first-order process that is not pH dependent in the physiological range of pHs. The half-life of this first order process depends on substitution on the aryl ring; the rate for benzenediazonium is ~4 hours. Indeed, the product of this degradation and subsequent azo-dye formation was observed if resorcinol is not put into the buffered NMR experiments.

In some embodiments, the acid-dependent instability of the triazabutadiene molecule may allow for a drug or cargo molecule to be deposited at a desired location and time (e.g., the reaction can be controlled and initiated at a desired time and location). As such, the present invention also features methods of delivering a drug (or a cargo compound) to a subject. In some embodiments, the method comprises providing a triazabutadiene molecule according to the present invention, conjugating a drug (or cargo compound) to the triazabutadiene molecule; and administering the conjugate (the drug/cargo-triazabutadiene conjugate) to the subject. In some embodiments, the method comprises providing a triazabutadiene molecule according to the present invention wherein the triazabutadiene molecule comprises the drug (or cargo compound); and administering the triazabutadiene molecule to the subject. In some embodiments, the diazonium species of the triazabutadiene molecule is part of the drug (or cargo compound). In some embodiments, the drug (or cargo compound) is formed when the diazonium species reacts to a phenol species. In some embodiments, the drug is an anti-cancer drug. The drug (or cargo compound) is not limited to an anti-cancer drug. Any appropriate drug for any appropriate condition may be considered. Likewise, the triazabutadiene molecules may be incorporated into drug/cargo-delivery systems for conditions including but not limited to cancer or other conditions associated with low pH states (e.g., gastrointestinal conditions, sepsis, ketoacidosis, etc.). Non-limiting examples of drugs (e.g., drugs that have a phenolic functional group, which may be masked as prodrugs) include: Abarelix, Alvimopan, Amoxicillin, Acetaminophen, Arformoterol, Cefadroxil, Cefpiramide, Cefprozil, Clomocycline, Daunorubicin, Dezocine, Epinephrine, Cetrolrelix, Etoposide, Crofelemer, Ezetimibe, Idarubicin, Ivacaftor, Hexachlorophene, Labetalol, Lanreotide, Levodopa, Caspofungin, Butorphanol, Buprenorphine, Dextrothyroxine, Doxorubicin, Dopamine, Dobutamine, Demeclocycline, Diflunisal, Dienestrol, Diethylstilbestrol, Doxycycline, Entacapone, Arbutamine, Apomorphine, Balsalazide, Capsaicin, Epirubicin, Esterified Estrogens, Estradiol Valerate, Estrone, Estradiol, Ethinyl Estradiol, Fulvestrant, Goserelin, Fluorescein, Indacaterol, Levosalbutamol, Levothyroxine, Liothyronine, Lymecycline, Mitoxantrone, Monobenzone, Morphine, Masoprocol, Mycophenolic Acid, Phenylephrine, Phentolamine, Oxytetracycline, Rifaximin, Rifapentine, Oxymetazoline, Raloxifene, Tolcapone, Terbutaline, Tetracycline, Mesalamine, Metaraminol, Methyldopa, Minocycline, Nabilone, Nalbuphine, Nelfinavir, Propofol, Rotigotine, Ritodrine, Salbutamol, Sulfasalazine, Salmeterol, Tapentadol, Tigecycline, Tolterodine, Teniposide, Telavancin, Topotecan, Triptorelin, Tubacurarine, Valrubicin, Vancomycin, etc.

In some embodiments, drug delivery systems featuring triazabutadiene molecules may be enhanced with other reactions, e.g., enzymatic reactions. Such additional reactions may help provide appropriate specificity of the drug delivery system or appropriate timing to the drug delivery system.

The present invention also features a method for administering a drug comprising a phenolic function group to a subject in need of such a drug administration. In some embodiments, the method comprises converting a drug comprising a phenolic-functional group to a prodrug, wherein said prodrug comprises an acid labile triazylidene moiety; and administering said prodrug to a subject in need of such a drug administration. In some embodiments, the triazylidene compound may also comprise a water solubility conferring moiety and/or $Y^1$ functional group.

The present invention also features a method of converting a drug comprising a phenolic-function group to an acid labile prodrug. In some embodiments, the phenolic-functional group is converted to an azide group. The azide functional group may then be reacted with a carbene to produce an acid labile prodrug comprising a triazylidene moiety.

In some embodiments, a triazabutadiene molecule is conjugated to another molecule (a conjugate molecule), e.g., a protein (e.g., an amino acid such as but not limited to lysine), a lipid, or other appropriate molecule. In some embodiments, the diazonium species part of the triazabutadiene molecule is conjugated to the conjugate molecule. In some embodiments, the cyclic guanidine species part of the triazabutadiene molecule is conjugated to the conjugate molecule. In some embodiments, the triazabutadiene molecule is attached to the conjugate molecule via a linker. Linkers are well known to one of ordinary skill in the art and may include (but are not limited to) a polyether linkers such as polyethylene glycol linkers. In some embodiments, the conjugate molecule to which the triazabutadiene molecule is conjugated comprises an antibody or a fragment thereof. In some embodiments, the conjugate molecule to which the triazabutadiene molecule is conjugated comprises a viral protein.

In some embodiments, the triazabutadiene molecules of the present invention are used for pull-down studies wherein a biomolecule or protein of interest is attached to one side and the other side is appended to something such as but not limited to a small molecule (e.g., hapten such as biotin) or compound. Using biotin as an example, the biomolecule or protein of interest can be pulled down using an avidin bead (which binds strongly to the biotin) and thoroughly washed. This may be useful for protein enrichment. The biomolecule or protein of interest may then be cleaved from the avidin bead by means of reductive cleavage of the triazabutadiene that holds them together. The present invention is not limited to these components, for example this application could also feature the use of a probe (e.g., fluorescent or otherwise) attached to an antibody used to interrogate a complex sample.

In some embodiments, reductive cleavage of triazabutadiene molecules may also be used to cleave unreacted triazabutadienes that did not undergo diazonium formation/reaction chemistry that is associated with a drop in pH (or other mechanism) as described above (a sort of quench for the pH chemistry).

As previously discussed, the diazonium species can react with a phenol species such as resorcinol or other appropriate phenol species. In some embodiments, a phenol species or resorcinol species is conjugated to a protein, e.g., a protein different from the protein to which the triazabutadiene molecule is conjugated, a protein that is the same protein to which the triazabutadiene molecule is conjugated, etc. In some embodiments, the resorcinol species or phenol species that the diazonium species reacts with is the phenol functional group of a tyrosine residue.

c. Other Applications

The present invention also features cross-linkers that respond to environmental triggers. This may allow for a chemical snapshot of a key moment of an interaction.

Example 1—Synthesis of a Fluorescent Triazabutadiene Probe

Example 1 describes transformation of a triazabutadiene into a fluorescent probe. The present invention is not limited to the compositions and methods described herein.

Figure 6:
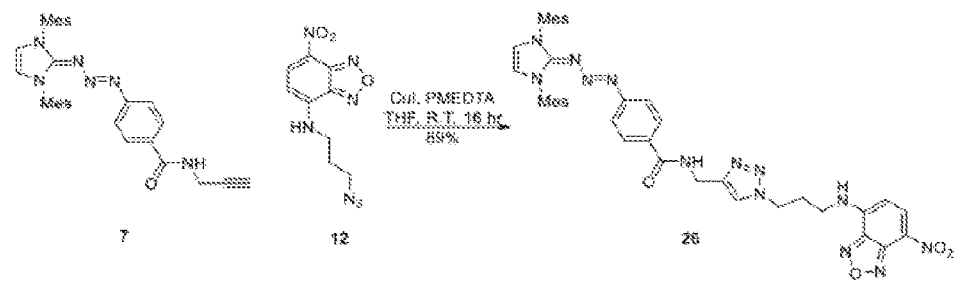
FIG. 6 shows synthesis of a fluorescent triazabutadiene.

Referring to FIG. 6, the fluorescent azide Compound 12 was coupled to the scaffold Compound 7. The yield of triazabutadiene Compound 26 was excellent. This modification added a component to the triazabutadiene by rendering the diazonium portion (upon appropriate cleavage of the triazabutadiene Compound 26) a fluorescent probe.

Example 2—Enhanced Functionalities of Triazabutadiene

Example 2 describes synthesis of a water-soluble triazabutadiene via click chemistry, a bi-functional triazabutadiene, and a triazabutadiene comprising an epoxide used to produce an alkyne handle. The present invention is not limited to the compositions and methods described herein.

Figure 7A:
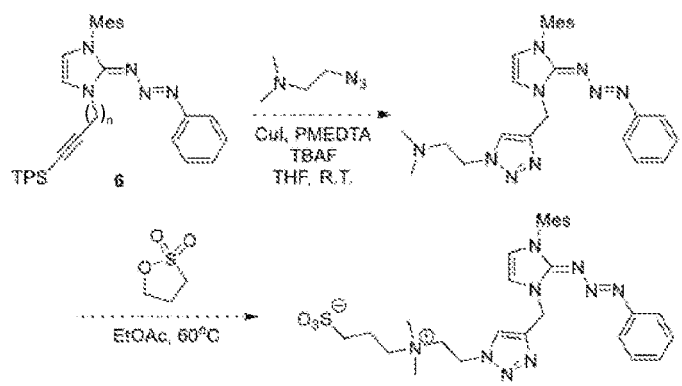
FIG. 7A shows synthesis of a water-soluble triazabutadiene via click chemistry. Note in some embodiments, n=1, n=2, n=3, n=4, etc.

Referring to FIG. 7A, in some embodiments, triazabutadienes may be made water soluble by attaching a water solubilizing agent or functional group to the triazabutadiene via click chemistry as described herein. For example, FIG. 7A shows formation of a triazole with a tertiary amine handle can undergo a nucleophillic attack on 1,3-propane sultone to synthesize a water-soluble zwitterionic triazabutadiene.

Figure 7B:
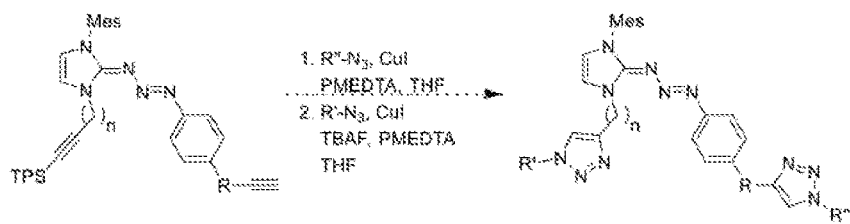
FIG. 7B shows a synthetic scheme of a bis-triazole-triazabutadiene. Note in some embodiments, n=1, n=2, n=3, n=4, etc.
Figure 8:
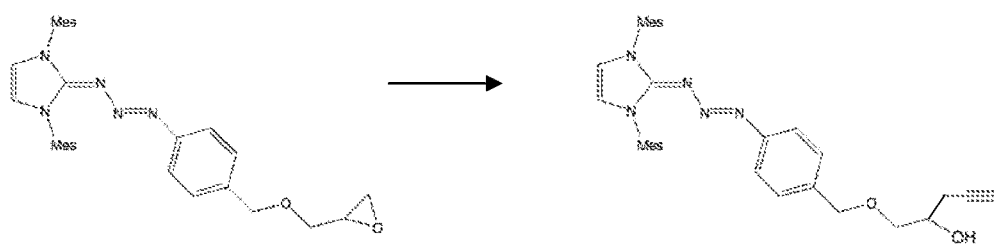
FIG. 8 shows a triazabutadiene comprising an epoxide (left) used to produce a triazabutadiene with an alkyne group adapted for click chemistry.

FIG. 7B shows a bis-alkynl triazabutadiene comprising two alkyne handles, one on the imidazole portion and one on the aryl portion (left side). The right side of the figure shows the two alkyne handles clicked via click chemistry with an azide group. A two-handled triazabutadiene can help enhance functionality of the triazabutadiene. For example, the two handles can be used to attach two different components (e.g., biological components, e.g., a protein, a drug, etc.). For example, in some embodiments, one side is used for a first biological component and the other side is used for a second biological component. In some embodiments, one side is used for a biological component and the other side is used for a water-solubilizing component. The present invention is not limited to the aforementioned attachment components or uses for a two-handled triazabutadiene. A In some embodiments, if one alkyne is protected, the other side could be preferentially used for clicking. FIG. 8 shows a triazabutadiene comprising an epoxide (left) used to produce a triazabutadiene with an alkyne group adapted for click chemistry.

The disclosures of the following documents are incorporated in their entirety by reference herein: U.S. Pat. No. 8,617,827; U.S. Pat. Application No. 2009/0048222; U.S. Pat. Nos. 3,591,575. 3,607,542; 4,107,353; WO Pat. No. 2008090554; U.S. Pat. No. 4,218,279; U.S. Pat. App. No. 2009/0286308; U.S. Pat. Nos. 4,356,050; 8,603,451; 5,856, 373; 4,602,073; 3,959,210. The disclosures of the following publications are incorporated in their entirety by reference herein: Kimani and Jewett, 2015, *Angewandte Chemie International Edition* (DOI: 10.1002/anie.201411277—Online ahead of print). Zhong et al., 2014, Nature Nanotechnology 9, 858-866; Stewart et al., 2011, J Polym Sci B Polym Phys 49(11):757-771; Poulsen et al., 2014, Biofouling 30(4):513-23; Stewart, 2011, Appl Microbiol Biotechnol 89(1):27-33; Stewart et al., 2011, Adv Colloid Interface Sci 167(1-2):85-93; Hennebert et al., 2015, Interface Focus 5(1):2014.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. Reference numbers recited in the claims are exemplary and for ease of review by the patent office only, and are not limiting in any way. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting of", and as such the written description requirement for claiming one or more embodiments of the present invention using the phrase "consisting of" is met.

The reference numbers recited in the below claims are solely for ease of examination of this patent application, and are exemplary, and are not intended in any way to limit the scope of the claims to the particular features having the corresponding reference numbers in the drawings.

What is claimed is:

1. A clickable triazabutadiene according to (a) Formula B wherein $X^1$ comprises a terminal azide handle; or (b) Formula C wherein either $X^1$ comprises a terminal azide, $X^2$ comprises a terminal azide handle, or both $X^1$ and $X^2$ comprise a terminal azide handle; wherein A=S, O, or N; D=H, —CH=CH—CH=E-, halides, cyano, sulfonates, alkyl chain, or trifluoromethyl; E=H, —CH=CH—CH=D-, halides, cyano, sulfonates, alkyl chain, or trifluoromethyl; and wherein $Y'$ comprises a tri-substituted aryl group; wherein the azide handles are adapted to cross-link to an alkyne handle of a linking component via click chemistry.

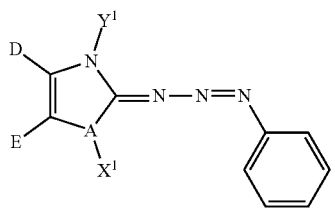

Formula B

-continued

Formula C

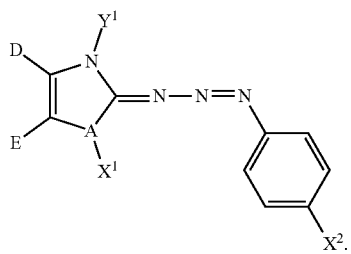

2. The clickable triazabutadiene of claim 1, wherein the tri-substituted aryl group comprises mesityl, a NHS-ester moiety; an oligonucleotide; a peptide; a fluorescence quencher; a pro-fluorophore; an alkyne; a triazene; an aldehyde; an amine; an aminooxy; a halogen; or a combination thereof.

3. The clickable triazabutadiene of claim 1, wherein the triazabutadiene comprises is linked to a peptide, an oligonucleotide, or a drug.

4. The clickable triazabutadiene of claim 1, wherein the linking component comprises a peptide, an oligonucleotide, or a drug.

5. A clickable triazabutadiene according to (a) Formula B wherein $X^1$ comprises a terminal azide handle or a terminal alkyne handle; or (b) Formula C wherein either $X^1$ comprises a terminal azide handle or a terminal alkyne handle, $X^1$ comprises a terminal azide handle or a terminal alkyne handle, or both $X^1$ and X comprise a terminal azide handle or a terminal alkyne handle; wherein A=S, O, or N; D=H, —CH═CH—CH═E-, halides, cyano, sulfonates, alkyl chain, or trifluoromethyl; E=H, —CH═CH—CH═D-, halides, cyano, sulfonates, alkyl chain, or trifluoromethyl; and wherein $Y^1$ comprises a tri-substituted aryl group; wherein azide handles are adapted to cross-link to an alkyne handle of a linking component via click chemistry or alkyne handles are adapted to cross-link to an azide handle of a linking component via click chemistry.

Formula B

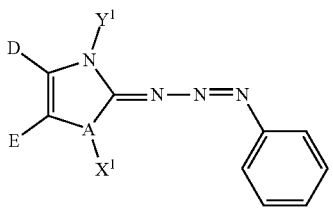

Formula C

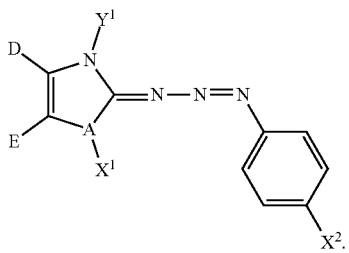

6. The clickable triazabutadiene of claim 5, wherein the tri-substituted aryl group comprises mesityl, a NHS-ester moiety; an oligonucleotide; a peptide; a fluorescence quencher; a pro-fluorophore; an alkyne; a triazene; an aldehyde; an amine; an aminooxy; a halogen; or a combination thereof.

7. The clickable triazabutadiene of claim 5, wherein the triazabutadiene comprises is linked to a peptide, an oligonucleotide, or a drug.

8. The clickable triazabutadiene of claim 5, wherein the linking component comprises a peptide, an oligonucleotide, or a drug.

* * * * *